(12) United States Patent
Löffler

(10) Patent No.: US 6,489,395 B2
(45) Date of Patent: Dec. 3, 2002

(54) EMULSIONS

(75) Inventor: Matthias Löffler, Niedernhausen (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/733,201

(22) Filed: Dec. 8, 2000

(65) Prior Publication Data

US 2001/0005737 A1 Jun. 28, 2001

(30) Foreign Application Priority Data

Dec. 8, 1999 (DE) .......................... 199 59 119

(51) Int. Cl.$^7$ .................. C08L 67/02; A61K 31/765
(52) U.S. Cl. ............... 524/845; 524/604; 524/815; 523/102; 424/78.03
(58) Field of Search ................ 524/604, 801, 524/845; 523/102; 424/78.03

(56) References Cited

U.S. PATENT DOCUMENTS

| | | | |
|---|---|---|---|
| 3,769,060 A | * | 10/1973 | Ida et al. |
| 3,962,152 A | | 6/1976 | Nicol et al. |
| 4,116,885 A | | 9/1978 | Derstadt et al. |
| 4,210,417 A | | 7/1980 | McClain et al. |
| 4,785,060 A | | 11/1988 | Nagler |
| 5,142,020 A | | 8/1992 | Kud et al. |
| 5,709,976 A | * | 1/1998 | Molhotra |
| 6,017,832 A | * | 1/2000 | Yahiaoui et al. |

FOREIGN PATENT DOCUMENTS

| | | |
|---|---|---|
| DE | 2 024 051 | 12/1971 |
| DE | 28 57 292 | 2/1980 |
| DE | 33 24 258 | 1/1984 |
| EP | 0 185 427 | 6/1986 |
| EP | 0 201 124 | 11/1986 |
| EP | 0 241 984 | 10/1987 |
| EP | 0 241 985 | 10/1987 |
| EP | 0 253 567 | 1/1988 |
| EP | 0 272 033 | 6/1988 |
| EP | 0 442 101 | 8/1991 |
| EP | 0 673 638 | 9/1995 |
| FR | 2 760 643 | 9/1998 |
| FR | 2 781 233 | 1/2000 |
| GB | 1 333 475 | 10/1973 |
| GB | 2 123 848 | 2/1984 |
| GB | 2 304 727 | 3/1997 |
| WO | 92/17523 | 10/1992 |

OTHER PUBLICATIONS

English abstract translation for FR 2760643, Sep. 18, 1998.
Chemical abstract XP–002169316, vol. 130, No. 1, Jan. 4, 1999, abstract No. 5129, "Optimised sil release polymers. Basic effects, detergency benefits, and interactions with detergent ingredients", Frank–Peter Lang, Bd, 16, Nr. 9, 1998.
English abstract translation for FR 2781233, Jan. 21, 2000.

* cited by examiner

Primary Examiner—Tae H. Yoon
(74) Attorney, Agent, or Firm—Richard P. Silverman

(57) ABSTRACT

Emulsions are claimed which comprise oligoesters as emulsifiers. These oligoesters have hitherto only been used as soil release polymers.

7 Claims, No Drawings

EMULSIONS

BACKGROUND OF THE INVENTION

It is known that oligoesters are used as soil release polymers in detergents and cleaners. These oligoesters are condensation products of dimethyl terephthalate, ethylene glycol, propylene glycol and polyalkylene glycols. As a consequence of a molar excess of the alcohol component, these oligoesters contain terminal OH groups which may, wholly or in part, be terminated by alkoxy groups (endcaps). Compounds of this type are available commercially under the names ®Milease T, ®Permalose, ®Repel-O-Tex. For more details, reference may be made to the specifications EP 185 427, EP 241 984, EP 241 985, EP 272 033, EP 757 468, EP 201 124, EP 253 567, GB 2 304 727, U.S. Pat. No. 4,116,885, U.S. Pat. No. 4,210,417, U.S. Pat. No. 3,962,152 and WO 92/17 523.

SUMMARY OF THE INVENTION

We have now found, surprisingly, that such oligoesters are also highly suitable as emulsifiers for emulsions.

The invention thus provides emulsions comprising an oligoester.

DESCRIPTION OF THE PREFERRED EMBODIMENTS

These oligoesters are preferably obtained by polycondensation of one or more aromatic dicarboxylic acids or esters thereof and one or more polyhydric alcohols, such as, for example, ethylene glycol and/or propylene glycol. Where appropriate, these esters can also contain polyethylene glycol, polypropylene glycol, sulfoisophthalic acid, sulfobenzoic acid, isethionic acid, $C_1$–$C_4$-alcohols, oxalkylated $C_1$–$C_{24}$-alcohols, oxalkylated $C_6$–$C_{18}$-alkylphenols and/or oxalkylated $C_8$–$C_{24}$-alkylamines as monomers.

Particular preference is given to emulsions comprising those oligoesters which have been obtained by polycondensation of a) 40 to 52 mol %, preferably 45 to 50 mol %, of one or more dicarboxylic acids or esters thereof, b) 10 to 60 mol %, preferably 20 to 35 mol %, of ethylene glycol and/or propylene glycol, c) 0 to 20 mol %, preferably 10 to 15 mol %, of polyethylene glycol, d) 0 to 10 mol % of a water-soluble addition product of from 5 to 80 mol of an alkylene oxide with 1 mol of $C_1$–$C_{24}$-alcohols, $C_6$–$C_{18}$-alkylphenols or $C_8$–$C_{24}$-alkylamines and e) 0 to 10 mol % of one or more polyols having 3 to 6 hydroxyl groups.

Suitable as component a) for the preparation of the oligoesters are aromatic dicarboxylic acids, such as, for example, terephthalic acid, phthalic acid, isophthalic acid, and the mono- and dialkyl esters with $C_1$- to $C_6$-alcohols, such as dimethyl terephthalate, diethyl terephthalate and di-n-propyl terephthalate. Further examples of compounds which can be used as component a) for the preparation of the polyesters are oxalic acid, succinic acid, glutaric acid, adipic acid, fumaric acid, maleic acid, itaconic acid, and the mono- and dialkyl esters of the carboxylic acids with $C_1$–$C_6$-alcohols, e.g. diethyl oxalate, diethyl succinate, diethyl glutarate, methyl adipate, diethyl adipate, di-n-butyl adipate, ethyl fumarate and dimethyl maleate. If the dicarboxylic acids which are suitable can form anhydrides, the anhydrides of the carboxylic acids having at least two carboxyl groups are also suitable as compound of component a) for the preparation of the oligoesters, e.g. maleic anhydride, phthalic anhydride or succinic anhydride. As compound of component a), particular preference is given to using terephthalic acid, phthalic acid, isophthalic acid, and the dimethyl, diethyl, dipropyl and dibutyl esters thereof. It is of course possible to use mixtures of different carboxylic acids or of different esters. Likewise, it is also possible to use, for example, mixtures of carboxylic acids and esters or mixtures of carboxylic acids and anhydrides in the condensation.

As component c), polyethylene glycols having molar masses of from 500 to 5000, preferably from 1000 to 3000, are used.

Suitable as component d) for the preparation of the oligoesters are water-soluble addition products of from 5 to 80 mol of at least one alkylene oxide with 1 mol of $C_1$–$C_{24}$-alcohols, $C_6$–$C_{18}$-alkylphenols or $C_8$–$C_{24}$-alkylamines. Preference is given to monomethyl ethers of polyethylene glycols. The alkylene oxides used for the preparation of the compounds of component d) are preferably ethylene oxide, and mixtures of ethylene oxide and propylene oxide. Also suitable are mixtures of ethylene oxide together with propylene oxide and/or butylene oxide, mixtures of ethylene oxide, propylene oxide and isobutylene oxide or mixtures of ethylene oxide and at least one butylene oxide. These water-soluble addition products of the alkylene oxide are surfactants. If mixtures of alkylene oxides are used for their preparation, then they may contain the alkylene oxides in blocks or else in random distribution.

Suitable alcohols which are alkoxylated are, for example, octyl alcohol, decyl alcohol, lauryl alcohol, myristyl alcohol or stearyl alcohol, but in particular methanol, and the alcohols having 8 to 24 carbon atoms obtainable by the Ziegler process, or the corresponding oxo alcohols. Of the alkylphenols, octylphenol, nonylphenol and dodecylphenol are of particular importance. The alkylamines used are, in particular, the $C_{12}$–$C_{18}$-monoalkylamines.

Suitable polyols (component e) are, for example, pentaerythritol, trimethylolethane, trimethylolpropane, 1,2,3-hexanetriol, sorbitol, mannitol and glycerol.

The oligoesters according to the invention are synthesized by processes known per se, by heating components a, b and c, and optionally d with the addition of a catalyst firstly at atmospheric pressure to temperatures of from 160 to about 220° C. The reaction is then continued under reduced pressure at temperatures of from 160 to about 240° C. with removal by distillation of excess glycols. The known transesterification and condensation catalysts of the prior art are suitable for the reaction, such as, for example, titanium tetraisopropoxide, dibutyltin oxide and/or antimony trioxide/calcium acetate. For further details on carrying out the process, reference is made to EP 442 101.

Also particularly suitable are the polyesters known from EP 241 985 which, in addition to oxyethylene groups and terephthalic acid units, contain 1,2-propylene, 1,2-butylene and/or 3-methoxy-1,2-propylene groups and glycerol units and are terminally capped with $C_1$- to $C_4$-alkyl groups; the soil release polymers, described in EP 253 567, having a molar mass of from 900 to 9000 g/mol of ethylene terephthalate and polyethylene oxide terephthalate, where the polyethylene glycol units have molecular weights of from 300 to 3000 g/mol and the molar ratio of ethylene terephthalate to polyethylene oxide terephthalate is 0.6 to 0.95; and the polyesters, known from EP 272 033, containing polypropylene terephthalate and polyoxyethylene terephthalate units and being at least proportionately terminally capped by $C_1$–$C_4$-alkyl radicals.

Likewise preferred are oligoesters of ethylene terephthalate and polyethylene oxide terephthalate in which the polyethylene glycol units have molecular weights of from 750 to 5000 g/mol and the molar ratio of ethylene terephthalate to polyethylene oxide terephthalate is 50:50 to 90:10 and whose use in detergents is described in German Patent Specification DE 28 57 292, and oligoesters having molecular weights of from 15 000 to 50 000 g/mol of ethylene terephthalate and polyethylene oxide terephthalate, where the polyethylene glycol units have molecular weights of from 1000 to 10 000 g/mol and the molar ratio of ethylene terephthalate to polyethylene oxide terephthalate is 2:1 to 6:1, which, according to DE 33 24 258, can be used in detergents.

Likewise preferred are the oligoesters described in DE 19 644 034 of the formula

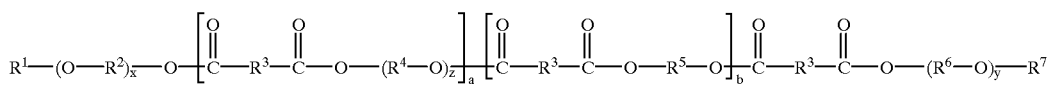

in which

R$^1$ and R$^7$ are linear or branched C$_1$- to C$_{18}$-alkyl,

R$^2$ and R$^6$ are ethylene,

R$^3$ is 1,4-phenylene,

R$^4$ is ethylene,

R$^5$ is ethylene, 1,2-propylene or random mixtures of any composition of the two, x and y independently of one another are numbers between 1 and 500, z is a number between 10 and 140, a is a number between 1 and 12, b is a number between 7 and 40, where a+b is at least 11.

Preferably, independently of one another,

R$^1$ and R$^7$ are linear or branched C$_1$- to C$_4$-alkyl, x and y are numbers between 3 and 45, z is a number between 18 and 70, a is a number between 2 and 5, b is a number between 8 and 12 and a+b is a number between 12 and 18 or between 25 and 35.
The oligoesters described in DE 19 644 034 are obtained from dimethyl terephthalate, ethylene glycol and/or propylene glycol, polyethylene glycol and C$_1$- to C$_{18}$-alkylpolyethylene glycol with the addition of a catalyst firstly by transesterification at temperatures of from 160 to about 220° C. and distillative removal of the methanol at atmospheric pressure and subsequent distillative removal of the excess glycols at temperatures of from 160 to about 240° C.

The described oligoesters are usually present in the emulsions according to the invention in amounts of from 0.1 to 5% by weight, preferably 0.3 to 3% by weight, based on the finished emulsion. The emulsions may either be water-in-oil emulsions or oil-in-water emulsions.

The nonaqueous proportion of the emulsions, which is composed largely of the emulsifier and the oil substance and generally corresponds to the solids content, is usually 5 to 95% and preferably 15 to 75% by weight. This means that the emulsions may comprise 5 to 95% by weight and preferably 25 to 85% by weight of water, depending on whether the intention is to prepare lotions of comparatively low viscosity, or creams and ointments of high viscosity.

Examples of suitable oil substances are Guerbet alcohols based on fatty alcohols having 6 to 18, preferably 8 to 10, carbon atoms, esters of linear C$_6$–C$_{13}$-fatty acids with linear C$_6$–C$_{20}$-fatty alcohols, esters of branched C$_6$–C$_{13}$-carboxylic acids with linear C$_6$–C$_{20}$-fatty alcohols, esters of linear C$_6$–C$_{18}$-fatty acids with branched alcohols, in particular 2-ethylhexanol, esters of linear and/or branched fatty acids with polyhydric alcohols (such as, for example, dimerdiol or trimerdiol) and/or Guerbet alcohols, triglycerides based on C$_6$–C$_{10}$-fatty acids, vegetable oils, branched primary alcohols, substituted cyclohexanes, Guerbet carbonates, dialkyl ethers and/or aliphatic or aromatic hydrocarbons.

The emulsions can be used as skin care compositions, such as, for example, day creams, night creams, care creams, nourishing creams, body lotions, ointments and the like, and can comprise, as further auxiliaries and additives, coemulsifiers, superfatting agents, fats, waxes, stabilizers, biogenic active ingredients, glycerol, preservatives, dyes and fragrances.

It is essential for the invention that the described oligoesters can also be used without the co-use of a nonionic surfactant as emulsifier. The co-use of emulsifiers is therefore not obligatory, but possible.

Suitable nonionogenic O/W coemulsifiers are addition products of from 2 to 30 mol of ethylene oxide and/or 0 to 5 mol of propylene oxide with linear fatty alcohols having 8 to 22 carbon atoms, with fatty acids having 12 to 22 carbon atoms and with alkylphenols having 8 to 15 carbon atoms in the alkyl group; C$_{12}$–C$_{18}$-fatty acid mono- and diesters of addition products of from 1 to 30 mol of ethylene oxide with glycerol; glycerol mono- and diesters and sorbitan mono- and diesters of saturated and unsaturated fatty acids having 6 to 22 carbon atoms and the ethylene oxide addition products thereof; addition products of from 15 to 60 mol of ethylene oxide with castor oil and/or hydrogenated castor oil; polyol and, in particular, polyglycerol esters, such as e.g. polyglycerol polyricinoleate and polyglycerol poly-12-hydroxystearate. Also suitable are mixtures of compounds of two or more of these classes of substance. The addition products of ethylene oxide and/or propylene oxide with fatty alcohols, fatty acids, alkylphenols, glycerol mono- and diesters, and sorbitan mono- and diesters of fatty acids or with castor oil are known, commercially available products. They are homolog mixtures whose average degree of alkoxylation corresponds to the ratio of the quantitative amounts of ethylene oxide and/or propylene oxide and substrate with which the addition reaction is carried out. C$_{12}$–C$_{18}$-fatty acid mono- and diesters of addition products of ethylene oxide with glycerol are known from DE 20 24 051 as refatting agents for cosmetic preparations.

Superfatting agents which can be used are substances such as, for example, polyethoxylated lanolin derivatives, lecithin derivatives, polyol fatty acid esters, monoglycerides and fatty acid alkanolamides, the latter also serving as foam stabilizers. Typical examples of fats are glycerides, and suitable waxes are, inter alia, beeswax, paraffin wax or microcrystalline waxes, optionally in combination with hydrophilic waxes, e.g. cetyl stearyl alcohol. Stabilizers which can be used are metal salts of fatty acids, such as e.g.

magnesium stearate, aluminum stearate and/or zinc stearate. Biogenic active ingredients means, for example, plant extracts and vitamin complexes. Examples of suitable preservatives are phenoxyethanol, formaldehyde solution, parabens, pentanediol or sorbic acid. Suitable pearlizing agents are, for example, glycol distearic esters, such as ethylene glycol distearate, but also fatty acid monoglycol esters. Dyes which can be used are the substances approved and suitable for cosmetic purposes, as are listed, for example, in the publication "Kosmetische Färbemittel" [Cosmetic Colorants] from the Farbstoffkommission der Deutschen Forschungsgemeinschaft [Dyes Commission of the German Research Council], Verlag Chemie, Weinheim, 1984, pp. 81–106.

The total proportion of auxiliaries and additives can be 1 to 10% by weight, preferably 2 to 5% by weight, based on the composition.

The compositions can be prepared in a manner known per se, i.e. for example by hot, hot-hot/cold or PIT emulsification.

Through the use according to the invention of the oligoesters in emulsions, in particular in O/W lotions and O/W creams, it is possible to obtain stable formulations which additionally impart a pleasant feel to the skin.

The examples below serve to illustrate the subject-matter of the invention in more detail, without limiting it thereto.

The following oligoesters according to the invention were used in the examples:

Polyester 1: 40 mol % of terephthalic acid, 10 mol % of ethylene glycol, 10 mol % of propylene glycol, 20 mol % of polyethylene glycol, 10 mol % of fatty alcohol ethoxylate, 10 mol % of polyol Polyester 2: 50 mol % of terephthalic acid, 25 mol % of ethylene glycol, 20 mol % of polyethylene glycol, 5 mol % of fatty alcohol ethoxylate Polyester 3: 50 mol % of hexanedicarboxylic acid, 40 mol % of propylene glycol, 10 mol % of polyethylene glycol These polyesters were prepared in the manner described in the introduction.

The following stability tests were carried out with the formulations described below:

Storage at 40° C., 45° C. and 50° C. over a period of 90 days.

Centrifugation at 20° C., 5000 rpm, 30 min

Under these conditions, all formulations exhibited good to very good stability.

EXAMPLE 1

O/W Cream

| | | |
|---|---|---|
| A | POLYESTER 1 (Clariant) | 1.00% |
| | ® Cetiol V | 7.00% |
| | Jojoba oil | 5.00% |
| | Isopropyl palmitate | 6.00% |
| B | ® Aristoflex AVC (Clariant) | 0.70% |
| C | Glycerol | 3.00% |
| | Water | 76.90% |
| | Preservative | q. s. |
| D | Perfume | 0.40% |

Preparation

I B was stirred into A, then C was added and stirred well

II D was added with stirring

III The emulsion was homogenized.

EXAMPLE 2

O/W Cream

| | | |
|---|---|---|
| A | POLYESTER 2 (Clariant) | 1.00% |
| | ® Cetiol V | 7.00% |
| | Jojoba oil | 5.00% |
| | Isopropyl palmitate | 6.00% |
| B | ® Aristoflex AVC (Clariant) | 0.70% |
| C | Glycerol | 3.00% |
| | Water | 76.90% |
| | Preservative | q. s. |
| D | Perfume | 0.40% |

Preparation: as in Example 1

EXAMPLE 3

O/W Cream

| | | |
|---|---|---|
| A | POLYESTER 1 (Clariant) | 1.50% |
| | Mineral oil, low-viscosity | 8.00% |
| | Isopropyl palmitate | 4.00% |
| | ® Eutanol G | 4.00% |
| B | ® Aristoflex AVC (Clariant) | 0.70% |
| C | Water | 81.40% |
| | Preservative | q. s. |
| D | Perfume | 0.40% |

Preparation: as in Example 1

EXAMPLE 4

O/W Cream

| | | |
|---|---|---|
| A | POLYESTER 2 (Clariant) | 1.00% |
| | Mineral oil, low-viscosity | 8.00% |
| | Isopropyl palmitate | 4.00% |
| | ® Eutanol G | 4.00% |
| B | ® Aristoflex AVC (Clariant) | 0.70% |
| C | Water | 81.90% |
| | Preservative | q. s. |
| D | Perfume | 0.40% |

Preparation: as in Example 1

EXAMPLE 5

O/W Sun Protection Milk

| | | |
|---|---|---|
| A | POLYESTER 1 (Clariant) | 1.00% |
| | Mineral oil, high-viscosity | 10.00% |
| | Isopropyl palmitate | 5.00% |
| B | ® Neo - Heliopan E 1000 | 8.50% |
| | ® Neo - Heliopan BB | 1.50% |
| C | Aristoflex AVC (Clariant) | 0.60% |
| D | Glycerol | 3.00% |
| | Water | 70.10% |
| | Preservative | q. s. |
| E | Perfume | 0.30% |

Preparation:
I B was mixed with A, then C was added
II D was added to the mixture I with stirring, then E was added,
III The emulsion was homogenized EXAMPLE 6
O/W Sun Protection Milk

| | | |
|---|---|---|
| A | POLYESTER 2 (Clariant) | 1.00% |
| | Mineral oil, high-viscosity | 10.00% |
| | Isopropyl palmitate | 5.00% |
| B | ® Neo - Heliopan E 1000 | 8.50% |
| | ® Neo - Heliopan BB | 1.50% |
| C | Aristoflex AVC (Clariant) | 0.60% |
| D | Glycerol | 3.00% |
| | Water | 70.10% |
| | Preservative | q. s. |
| E | Perfume | 0.30% |

Preparation: as in Example 5

EXAMPLE 7
O/W Sun Protection Milk

| | | |
|---|---|---|
| A | POLYESTER 3 (Clariant) | 2.00% |
| | Mineral oil, high-viscosity | 10.00% |
| | Isopropyl palmitate | 5.00% |
| B | ® Neo - Heliopan E 1000 | 8.50% |
| | ® Neo - Heliopan BB | 1.50% |
| C | Aristoflex AVC (Clariant) | 0.60% |
| D | Glycerol | 3.00% |
| | Water | 69.10% |
| | Preservative | q. s. |
| E | Perfume | 0.30% |

Preparation: as Example 5

Chemical names of the commercial products used:
Aristoflex AVC: Acrylamidopropylenesulfonic acid/vinylformamide copolymer
Cetiol: Decyl oleate
Eutanol G: Hexyldecanol
Neo-Heliopan E 1000: Isoamyl p-methoxycinnamate
Neo-Heliopan BB: Benzophenone-3

What is claimed is:

1. A skin cosmetic emulsion comprising an emulsifier comprising oligoesters obtained by polycondensation of
    a) 40 to 52 mol % of one or more aromatic dicarboxylic acids or esters thereof,
    b) 10 to 60 mol % of ethylene glycol and/or propylene glycol,
    c) 0 to 20 mol % of polyethylene glycol,
    d) 0 to 10 mol % of a water-soluble addition product of from 5 to 80 mol of an alkylene oxide with 1 mol of a component selected from the group consisting of $C_1$–$C_{24}$-alcohols, $C_6$–$C_{18}$-alkylphenols, and $C_8$–$C_{24}$-alkylamines and
    e) 0 to 10 mol % of one or more polyols having 3 to 6 hydroxyl groups wherein said cosmetic emulsion further comprises oils, superfatting agents, preservatives and fragrances.

2. The skin cosmetic emulsion as claimed in claim 1, which comprises 0.1 to 5% by weight of said emulsifier.

3. The skin cosmetic emulsion as claimed in claim 1 wherein the oligoesters are obtained by polycondensation of 45 to 50 mol % of one or more aromatic dicarboxylic acids or esters thereof.

4. The skin cosmetic emulsion as claimed in claim 1 wherein the oligoesters are obtained by polycondensation of said aromatic dicarboxylic acids or esters thereof and 20 to 35 mol % of ethylene glycol and/or propylene glycol.

5. The skin cosmetic emulsion as claimed in claim 1 wherein the oligoesters are obtained by polycondensation of said aromatic dicarboxylic acids or esters thereof, said ethylene glycol and/or propylene glycol, and 10 to 15 mol % of polyethylene glycol.

6. A skin cosmetic emulsion comprising an emulsifier comprising oligoesters obtained by polycondensation of
    a) 40 to 52 mol % of one or more aromatic dicarboxylic acids or esters thereof,
    b) 10 to 60 mol % of ethylene glycol and/or propylene glycol,
    c) 0 to 20 mol % of polyethylene glycol,
    d) 0 to 10 mol % of a water-soluble addition product of from 5 to 80 mol of alkylene oxide with 1 mol of a component selected from the group consisting of $C_1$–$C_{24}$-alcohols, $C_6$–$C_{18}$-aikylphenols, and $C_8$–$C_{24}$-alkylamines and
    e) 0 to 10 mol % of one or more polyols having 3 to 6 hydroxyl groups
    wherein said cosmetic emulsion further comprises superfatting agents, fats, waxes, stabilizers, biogenic active ingredients, glycerol, preservatives, dyes and fragrances.

7. The skin cosmetic emulsion of claim 6 wherein the aromatic dicarboxylic acids or esters thereof are selected from the group consisting of terephthalic acid, phthalic acid, isophthalic acid, and the dimethyl, diethyl, dipropyl and dibutyl esters thereof.

* * * * *